United States Patent [19]
Matsuura

[11] Patent Number: 5,820,902
[45] Date of Patent: Oct. 13, 1998

[54] PHYSIOLOGICALLY ACTIVE AGENT FOR FISH AND FEED ADDITIVE FOR FISH CULTIVATION

[75] Inventor: Akihisa Matsuura, Komatsu, Japan

[73] Assignee: Araya Corporation, Ishikawa, Japan

[21] Appl. No.: 714,530

[22] Filed: Sep. 16, 1996

[30] Foreign Application Priority Data

Sep. 18, 1995 [JP] Japan .................................. 7-264938

[51] Int. Cl.$^6$ .......................... A01H 63/02; A61K 35/74; A23K 1/00; A23C 9/12
[52] U.S. Cl. .......................... 426/61; 424/93.4; 424/115; 426/2; 426/805; 435/41; 435/252.1; 435/822
[58] Field of Search .................................. 435/41, 252.1, 435/822; 426/2, 61; 424/115, 93.4, 805

[56] References Cited

U.S. PATENT DOCUMENTS

| | | | |
|---|---|---|---|
| 4,616,039 | 10/1986 | Herschler | 514/711 |
| 4,914,135 | 4/1990 | Herschler | 514/711 |

OTHER PUBLICATIONS

APS Abstract Japan 08–70785 Matsuura et al Mar. 19, 1996.

*Primary Examiner*—Herbert J. Lilling
*Attorney, Agent, or Firm*—Armstrong, Westerman, Hattori, McLeland, & Naughton

[57] ABSTRACT

A physiologically active agent for fish is provided which comprises metabolite of green sulfur bacteria as an effective component thereof. The physiologically active agent, which can be easily prepared by the mass culture of green sulfur bacteria, exhibits an excellent efficiency as a feed additive, can be preserved for a long time and hence is economical.

10 Claims, 1 Drawing Sheet

PHYSIOLOGICALLY ACTIVE AGENT FOR FISH AND FEED ADDITIVE FOR FISH CULTIVATION

BACKGROUND OF THE INVENTION

1. Field of the Invention

The present invention relates to physiologically active agents for fish and feed additives for fish cultivation.

2. Related Art

Green sulfur bacteria have been worked on the development as feed additives in the cultivation of fishes such as eel, loach, sweetfish, fluke, red sea bream and prawn and, especially, for the young thereof. These feed additives have been proved to exhibit effectiveness in increasing the feed efficiency.

However, when the green sulfur bacteria cells are added, these feed additives are liable to decompose by the green sulfur bacteria, resulting in deterioration in two or three months. In view of the foregoing, there have been desired to find physiologically active agents for fish and feed additives for fish cultivation of other kinds that can be preserved for a long time by removing the cause of decay.

SUMMARY OF THE INVENTION

To solve the aforesaid problems, the inventor of the present invention has intensively investigated metabolites of green sulfur bacteria and found that metabolites of the green sulfur bacteria contains an effective component for promoting the growth of fish more than the green sulfur bacteria cells containing an effective component, and found a means for obtaining physiologically active agents for fish and feed additives for fish cultivation in extracting the effective component. In accordance with the present invention, a physiologically active agent for fish and a feed additive for fish cultivation are provided which can be easily mass-produced, and are excellent in feed additive efficiency and can be preserved for very long term, and are hence economical.

Thus, the present invention provides a physiologically active agent for fish comprising metabolite of the green sulfur bacteria as an effective component thereof.

The present invention also provides a feed additive for culture fish comprising the aforesaid physiologically active agent.

It is, therefore, an object of the present invention to provide the physiologically active agent for fish comprising the metabolites of the green sulfur bacteria as an effective component.

DESCRIPTION OF THE PREFERRED EMBODIMENTS

Figure 1:
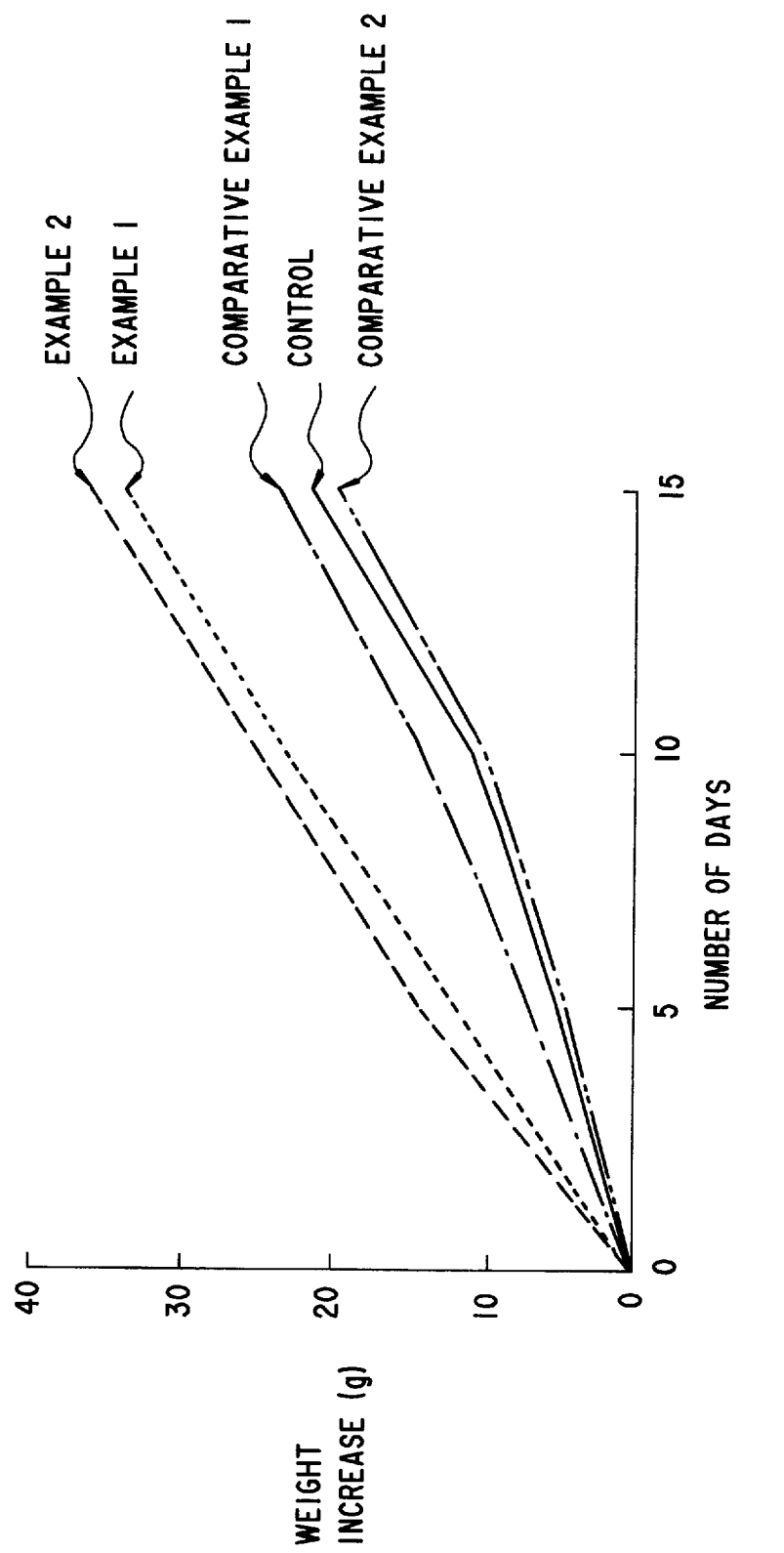
FIG. 1. shows the relationship between the weight increase and the number of test days.

The metabolites of the green sulfur bacteria can be obtained as follows.

Bacteria are removed by filtering a cultured medium solution containing the green sulfur bacteria, and the filtrate containing only metabolites of the green sulfur bacteria and culture medium components are obtained, and further the culture medium components of salts and the like are removed, and the metabolite can be obtained.

One of the reasons for the removal of culture medium components is that, in keeping dry, for example freeze-dry etc., culture medium components appear as many salts, and the recovery rate of effective components becomes poor. Another reason is that, culture medium components do not include components which are available for physiological activity for fish.

Examples of methods include a method of removing only low-molecular weight components cultured medium by reverse osmotic membrane or ultrafiltration membrane. These methods are effective, because it is estimated that the components of metabolites which are effective in promoting a growth have an average molecular weight of 200 or more. However, the present invention is not limited to these methods. The period of time required for culturing the green sulfur bacteria in the present invention is short. Typically, the green sulfur bacteria proliferate into a high concentration of more than $10^9$/ml within 24 hours. The culture medium for the green sulfur bacteria is less costly, and the mass production thereof is easy and economical. The green sulfur bacteria can be stably cultured without a fear of proliferation of unwanted microbes even if sterilization and aseptic operation are omitted in the subculture step. Further, the green sulfur bacteria do not cause any ingestion deterrence nor toxicity to fish, but rather are proved to mark a notable improvement in the ingestion and growth promotion. From the foregoing findings, the culture medium for the green sulfur bacteria is the most suitable as a feed additive for fish. Even if the metabolite of the green sulfur bacteria are separated and extracted and added as a feed additive, the metabolite are still effective and can be preserved for a long time.

In general, the green sulfur bacteria are green photosynthetic bacteria which anaerobically carry out photosynthesis using hydrogen sulfide, colloidal sulfur, thiosulfates and molecular hydrogen as an electron donor, and are capable of living only by way of photosynthesis without requiring any growth factor. The green sulfur bacteria have a photosynthesis system in an independent vesicle structure within each cell thereof, which system contains a small amount of bacteriochlorophills as well as chlorobium chlorophylls. Energy transfer occurs between these two pigments. Green sulfur bacteria belonging to genus Chlorobium perform assimilation under such a condition that a small amount of acetic acid coexists with $H_2S$.

The present invention reveals that the metabolites of the green sulfur bacteria is more effective than the green sulfur bacteria themselves, at the same time, proves that the green sulfur bacteria, when used as a physiologically active agent, remarkably contribute to an improvement in an ingestion capability of fish, thereby improving the feed efficiency.

Exemplary green sulfur bacteria in accordance with the present invention include *Chlorobium limicola* (DSM 245), *Chlorobium vibrioforme* (DSM260), *Chlorobium phaeobacteroides* (DSM266), *Chlorobium phaeovibrioides* (DSM269), *Prosthecochloris aestualii* (DSM 271), *Chlorobium tepidum* (ATCC 49652), *Pelodictyon luteolum* (DSM 273), *Pelodictyon phaeum* (DSM 728), and any other green sulfur bacteria which can be artificially cultured. Particularly preferable among these are green sulfur bacteria belonging to the genus Chlorobium because they are suitable for mass culture.

The temperature and pH conditions for culture vary depending on the species of the green sulfur bacteria and their favorite proliferation conditions. As fundamental conditions for a preferable culture of the green sulfur bacteria, a culture medium for the green sulfur bacteria is prepared such that the pH thereof is a little acidic (typically, within a pH range of about 7.5 to about 6.3), and the illumination on the surface of a culture vessel is adjusted to not lower than 2000 Lux. Preferably, the culture is carried out under an absolute anaerobic condition at a temperature of between about 20° C. and about 30° C. with the culture medium containing sodium acetate added as an organic component thereto in a concentration of about 0.05%.

Examples of feeds for fish cultivation include raw feed such as krill, and assorted feed containing a fish meal, starch or the like as a main ingredient thereof and a thickener, vitamins, minerals and the like as additives. The feed is generally supplied to fish in the form of paste or pellet. When cultured medium that contains metabolites of the green sulfur bacteria and is filtrated for removing bacterial cells, or cultures that contain the bacterial cells or these mixtures are added to a feed as a feed additive for fish, the culture medium containing the green sulfur bacteria or the bacteria themselves are diluted with water or undiluted, and then added to and mixed with the feed paste. The feed pellets may be impregnated with the culture medium.

The application of the green sulfur bacteria used in the present invention is not limited to a feed additive for fish cultivation. For example, the green sulfur bacteria or metabolite thereof, which contain vitamins, minerals, amino acids and the like, can also be used as a nutrient. In brief, the green sulfur bacteria or the metabolites thereof can be effectively applied as a physiologically active agent for fish.

The proportion of the green sulfur bacteria to be added to the feed is preferably about 0.1% by weight, if used in a dried form. If the culture medium containing the green sulfur bacteria is used, the proportion of the medium solution to be added to the feed is preferably about 1% to about 50% which depends on a bacterial concentration of the cultered medium. A bacteria proportion lower than the aforesaid value results in little improvement in ingestion. Even if the bacterial proportion is higher than the aforesaid value, any extra effect cannot be expected.

The present invention relates to a physiologically active agent for fish comprising the green sulfur bacteria and metabolites thereof as effective components. The feed containing the physiologically active agent as a feed additive for fish cultivation effectively improves the growth rate. The green sulfur bacteria proliferate into a high concentration of more than $10^9$/ml within 24 hours, compared with oter bacteria. The medium for cultivation of the green sulfur bacteria is less costly, and the mass production thereof is easy and economical. The green sulfur bacteria can be stably cultured without a fear of proliferation of unwanted microbes even if sterilization and aseptic operation are omitted in the subculture step. Further, the green sulfur bacteria cause neither any ingestion deterrence nor toxicity to fish, but rather are proved to mark a notable improvement in the ingestion and growth promotion. However, when the green sulfur bacteria are being left, they are liable to decay and become deteriorated in two or three months even if they have been preserved at 4° C. or less. Therefore, the metabolite thereof only is separated by filtering by 0.2 µm membrane filter and resulting in removal of the cause of decay that is bacteria themselves, so that they can be preserved for long periods.

With consideration of preservation, a physiologically active agent for fish and a feed additive for fish cultivation comprising the metabolites of the green sulfur bacteria as an effective component thereof are preferable in the present invention.

On the other hand, without consideration of preservation, it is safe to say that a physiologically active agent for fish and a feed additive for fish cultivation comprise the bacterial cells, or culture medium containing green sulfur bacteria without removing the metabolites of the green sulfur bacteria as an effective component thereof.

When a physiologically active agent for fish and a feed additive for fish cultivation comprise the metabolites of the green sulfur bacteria and the bacterial cells as effective components thereof, they can improve yields better than when they comprise only metabolite of green sulfur bacteria, and can exhibit synergistic action of physiological activity.

EXAMPLES 1 AND 2

Five containers of 30 cm×30 cm×30 cm were filled with water. Then, 15 goldfish were put in each of the containers and cultivated to the total weight 77.0 g.

For a control test, feed for goldfish (ANGEL FLOAT (brand name) available from NIPPON PET FOODS Co.) were supplied to the container.

For EXAMPLE 1, feed and cultured medium containing *Chlorobium limicola* filtrated (not including the bacterial cells) at a rate of about 5% of the weight of the goldfish were individually supplied to the container per day. The concentration of the cultured medium was about 4% by weight relative to the total weight of the feed for goldfish.

Five test sections were prepared: (a) a section supplied with a feed and about 4% cultured medium containing *Chlorobium limicola* filtrated (not including bacterial cells) relative to the total weight of the feed for goldfish. (for EXAMPLE 1) (b) a section supplied with only a feed for goldfish. (for control) (c) a section supplied with a feed and about 4% cultured medium containing for *Chlorobium limicola* (including the bacterial cells) relative to the total weight of the feed for goldfish. (for EXAMPLE 2) (d) a section supplied with a feed and the bacterial cells that were filtered and cleaned by 0.2 µm membrane filter from the same amount of the cultured medium as EXAMPLE 2. (for COMPARATIVE EXAMPLE 1) (e) a section supplied with a feed and about 4% culture medium for the green sulfur bacteria as above. (for COMPARATIVE EXAMPLE 2)

The following Table 1 shows the weight after the tests.

TABLE 1

| | Total weight (g) | | | | |
|---|---|---|---|---|---|
| | EX. 1 | control | EX. 2 | COMP. EX. 1 | COMP. EX. 2 |
| Initial weight | 77.0 | 77.0 | 77.0 | 77.0 | 77.0 |
| Weight after 5 days | 89.2 | 82.1 | 91.5 | 84.3 | 81.6 |
| Weight after 10 days | 100.1 | 88.9 | 102.1 | 91.4 | 87.4 |
| Weight after 15 days | 110.9 | 98.7 | 113.3 | 100.7 | 96.9 |

The growth in COMPARATIVE EXAMPLE 1 was slightly better than the growth in control test, however, the growth in both of EXAMPLE 1 and EXAMPLE 2 were remarkably improved.

It was found that the culture medium had no effectiveness, because the growth in COMPARATIVE EXAMPLE 2 was poor compared to the growth in control test.

The following Table 2 shows the weight increase during the tests.

TABLE 2

| | EX. 1 | control | EX. 2 | COMP. EX. 1 | COMP. EX. 2 |
|---|---|---|---|---|---|
| Initial weight increase | 0.0 | 0.0 | 0.0 | 0.0 | 0.0 |
| Weight increase after 5 days | 12.2 | 5.1 | 14.5 | 7.3 | 4.6 |
| Weight increase after 10 days | 23.1 | 11.9 | 25.1 | 14.4 | 10.4 |
| Weight increase after 15 days | 33.9 | 21.7 | 36.3 | 23.7 | 19.9 |

Table 2 compares the weight increase [(the total weight after n days)−(initial total weight, 77.0 g)]. This table shows an increase in weight of EXAMPLE 1 and EXAMPLE 2.

FIG. 1 shows the relationship between the weight increase and the number of test days based on Table 2.

EXAMPLES 3 AND 4

Four containers of 75 cm×45 cm×45 cm were filled with water. Then, 60 young red sea breams (the average weight 0.2 g) were put in each of the containers and cultivated for one month.

For a control test, feed for red sea bream were supplied to the container.

Four test sections were prepared: (a) a section supplied with only a feed for red sea bream. (for control) (b) a section supplied with a feed containing about 2% culture medium solution containing *Chlorobium limicola* (including bacterial cells) relative to the total weight of the feed for red sea bream. (for EXAMPLE 3) (c) a section supplied with a feed containing about 2% of the filtered cultured medium of the *Chlorobium limicola* by using 0.2 μm membrane filter (not including the bacterial cells) relative to the total weight of the feed for red sea bream. (for EXAMPLE 4) (d) a section supplied with a feed containing only the bacterial cells that were filtered and cleaned with 0.2 μm membrane filter from the same amount of the culture medium solution as EXAMPLE 4 (for COMPARATIVE EXAMPLE 3)

Table 3 shows a feed efficiency and a survival rate.

TABLE 3

| | control | EX. 3 | EX. 4 | COMP. EX. 3 |
|---|---|---|---|---|
| Initial weight (g) | 12.0 | 12.0 | 12.0 | 12.0 |
| Weight after test (g) | 264.0 | 300.0 | 289.0 | 266.0 |
| Weight increase (g) | 252.0 | 288.0 | 277.0 | 254.0 |
| Feed amount (g) | 239.0 | 239.0 | 239.0 | 239.0 |
| Feed efficiency (%) | 105.4 | 120.5 | 115.9 | 106.3 |
| Weight increase rate (%) | 2200 | 2500 | 2408 | 2217 |
| Number of survived fish after test | 54 | 59 | 56 | 59 |
| Survival rate (%). | 90.0 | 98.3 | 93.3 | 98.3 |

In the Table 3, the initial weight means the total weight (g) of red sea bream at the beginning of the test, the weight after test means the total weight (g) of the red sea bream at the end of the test, the weight increase means [(weight after test)−(initial weight)] (g), the feed amount means the total amount (g) of feed supplied during the test, the feed efficiency means [(weight increase)/(feed amount)×100] (%), the weight increase rate means [(weight after test)/(initial weight)×100] (%), and the survival rate means [(the number of survived fish after test)/60)×100] (%).

As a result of this, the growth in EXAMPLE 3 and EXAMPLE 4 were good. The survival rate during the test was 98.3%(EXAMPLE 3), 93.3%( EXAMPLE 4) and 98.3% (COMPARATIVE EXAMPLE 3 compared with 90.0% (control), and the improvement in the survival rate was observed.

*Chlorobium limicola* was used in the examples as green sulfur bacteria. The *Chlorobium limicola* was cultured at a temperature of 30° C. with an illumination of 5000 Lux for one day in a culture medium having a pH of 6.8±0.2 and containing: 0.5 g of dipotassium phosphate, 0.5 g of ammonium sulfate, 0.2 g of magnesium sulfate, 0.05 g of calcium chloride, 0.1 g of sodium chloride, 1.0 g of sodium bicarbonate, 1.0 g of sodium sulfide, 1.0 g of sodium thiosulfate, a trace amount of EDTA, a trace amount of EDTA-iron salt, a trace amount of EDTA-cobalt salt, a trace amount of boric acid, a trace amount of cupric sulfate, a trace amount of zinc sulfate, a trace amount of sodium molybdate, a trace amount of nickel chloride, a trace amount of manganese chloride, and 1000 ml of water.

In the foregoing examples of the present invention, the goldfish and young red sea bream are used, but not limited thereto. The metabolites of the green sulfur bacteria cause neither ingestion deterrence nor toxicity to fish, but rather improves the ingestion, thereby promoting the growth of fish. In addition, the time period required for culturing the green sulfur bacteria under predetermined conditions is short. Even culture medium solution filtrated have a sufficient efficiency in promoting the growth of fish, i.e. Further, the culture medium for the green sulfur bacteria is less costly, and the mass production of the bacteria is easy and economical. Still further, the green sulfur bacteria can be stably cultured without a fear of proliferation of unwanted microbes even if sterilization and aseptic operation are omitted in the subculture step. Thus, the present invention is directed to take these advantages. Therefore, the present invention is applicable to generally all kinds of fish, i.e., not only fresh-water fish but also salt-water fishes.

Such green sulfur bacteria as *Chlorobium limicola* (DSM 245)was used in Examples and improved the feed efficiency and the weight increase rate. Similarly, *Chlorobium vibrioforme* (DSM 260), *Chlorobium phaeobacteroides* (DSM 266), *Chlorobium phaeovibrioides* (DSM 269), *Prosthecochloris aestualii* (DSM 271), *Chlorobium tepidum* (ATCC 49652), *Pelodictyon luteolum* (DSM 273) and *Pelodictyon phaeum* (DSM 728) can improve the feed efficiency and the weight increase rate.

As can be seen from the foregoing, the present invention provides a physiologically active agent for fish comprising the metabolite of the green sulfur bacteria as an effective component thereof. The feed containing the physiologically active agent as a feed additive for fish cultivation effectively improves the preservation and the growth promotion, compared with the feed containing only the the bacterial cells. Furthermore, the culture period of the green sulfur bacteria is very short, i.e., the green sulfur bacteria can be cultured into a high concentration in a short time, and the culture medium required therefor is less costly. Therefore, the physiologically active agent including the metabolite of green sulfur bacteria is extremely suitable for mass production. Further, the physiologically active agent cause neither ingestion deterrence nor toxicity to fish, but rather improves the ingestion of fish and provides a very high efficiency as a feed additive.

What is claimed is:

1. A physiologically active agent for fish comprising as an effective component thereof metabolites which are obtained by filtering a cultured broth of a green sulfur bacterium with a filter.

2. The physiologically active agent for fish of claim 1, wherein the green sulfur bacterium belongs to Genus Chlorobium.

3. The physiologically active agent of claim 1, wherein the green sulfur bacterium is selected from the group consisting of *Chlorobium limicola, Chlorobium vibrioforme, Chlorobium phaeobacteroides, Chlorobium phaeovibrioides, Prosthecoloris aestualii, Chlorobium tempidum, Pelodictyon luteolum* and *Pelodictyon phaeum*.

4. The physiologically active agent of claim 1, wherein the green sulfur bacterium is *Chlorobium limicola*.

5. A feed additive for fish cultivation comprising as an effective component thereof metabolites which are physiologically active for fish and obtained by filtering cultured broth of a green sulfur bacterium with a filter.

6. The feed additive for fish cultivation of claim 5 comprising as an effective component thereof a cultured broth of the green sulfur bacterium that contains metabolites which are physiologically active for fish.

7. The feed additive for fish cultivation of claim 6, wherein the cultured broth contains cells of the green sulfur bacterium.

8. The feed additive of claim 6 wherein the green sulfur bacterium belongs to Genus Chlorobium.

9. The feed additive of claim 8, wherein the green sulfur bacterium is selected from the group consisting of *Chlorobium limicola, Chlorobium vibrioforme, Chlorobium phaeobacteroides, Chlorobium phaeovibrioides, Prosthecoloris aestualii, Chlorobium tempidum, Pelodictyon luteolum* and *Pelodictyon phaeum*.

10. The feed additive of claim 8, wherein the green sulfur bacterium is *Chlorobium limicola*.

\* \* \* \* \*